United States Patent [19]

Ishiwatari

[11] Patent Number: 4,556,875
[45] Date of Patent: Dec. 3, 1985

[54] IRRADIATED POWER MONITORING SYSTEM FOR OPTICAL FIBER

[75] Inventor: Hiromasa Ishiwatari, Ikoma, Japan

[73] Assignee: Matsushita Electric Industrial Co., Ltd., Kodoma, Japan

[21] Appl. No.: 444,331

[22] Filed: Nov. 24, 1982

[30] Foreign Application Priority Data

Dec. 15, 1981 [JP] Japan .................................. 56-203272
Dec. 15, 1981 [JP] Japan .................................. 56-203273

[51] Int. Cl.⁴ ............................................ G08B 21/00
[52] U.S. Cl. .................................. 340/679; 128/303.1;
219/121 LB; 340/540; 340/555; 340/557;
356/73.1; 455/610
[58] Field of Search ................................ 340/555–557,
340/679, 540, 654; 128/23, 397, 398, 303.1, 395,
396; 356/73.1; 350/96.33, 96.24; 455/610, 612;
250/205; 219/121 L, 121 LA, 121 LB, 121 LX

[56] References Cited

U.S. PATENT DOCUMENTS

| 2,047,665 | 7/1936 | Beggs | 340/556 X |
|---|---|---|---|
| 2,595,993 | 5/1952 | Templeman et al. | 340/556 X |
| 3,678,492 | 7/1972 | Casper | 340/555 |
| 3,683,352 | 8/1972 | West et al. | 340/557 |
| 3,689,159 | 9/1972 | Taniguchi et al. | 219/121 LX X |
| 3,825,916 | 7/1974 | Steele et al. | 340/557 |
| 3,852,592 | 12/1974 | Scoville et al. | 340/555 X |
| 3,987,428 | 10/1976 | Todeschini | 340/557 |
| 4,134,642 | 1/1979 | Kapron et al. | 350/96.33 |
| 4,311,142 | 1/1982 | Machida | 340/557 X |
| 4,385,832 | 5/1983 | Doi et al. | 356/73.1 |
| 4,399,565 | 8/1983 | Jarret et al. | 340/556 X |
| 4,459,986 | 7/1984 | Karaki | 128/303.1 |

OTHER PUBLICATIONS

"Field Disturbance Sensing Unit", K. E. Powell, *IBM Technical Disclosure Bulletin*, vol. 18, No. 7, pp. 2275–2276, Dec. 1975.

*Primary Examiner*—Charles A. Ruehl
*Assistant Examiner*—Thomas J. Mullen, Jr.
*Attorney, Agent, or Firm*—Cushman, Darby & Cushman

[57] ABSTRACT

In a laser working apparatus comprising a large power laser oscillator, laser light beam conducting means, and a hand-piece with which the output laser light beam from said conducting means is emanated on desired objectives. The hand-piece comprises a convergence lens for focusing the output light to the desired object and a light detecting means disposed in a casing of the hand-piece, so as to detect the outskirt portion of the converged light beam, which is not utilized for the working, thereby the output laser light is continuously checked for its existence or for its intensity, to assure a reliable operation. By such a detection means, many troubles or defects of the light conducting means are continuously watched.

7 Claims, 10 Drawing Figures

IRRADIATED POWER MONITORING SYSTEM FOR OPTICAL FIBER

BACKGROUND OF THE INVENTION

1. Field of the Invention

The present invention relates to an irradiated power monitoring system for optical fiber for use in laser working apparatus or laser surgical operation apparatus.

The present invention particularly concerns an irradiated power monitoring system for optical fibers having high reliability without interrupting laser working or laser surgical operation.

2. Description of the Prior Art

The conventional laser working apparatus or laser surgical operation apparatus utilizing a laser beam of a $CO_2$ laser have used mirror joint waveguide means for guiding the laser beam from the laser oscillator to an object working point. However, the mirror articulated waveguide has problems such as, the deviation of light beam from the designated path due to vibration of the mirrors and arms or inconvenience of handling. Accordingly, in order to solve such problems in the conventional laser working apparatus or laser surgical operation apparatus, use of optical fibers as a laser beam waveguide has been tried. FIG. 1 shows the inventor's experimental apparatus using the optical fiber as the laser beam waveguide in a schematic way. Laser light beam 5 emitted from the laser oscillator 1 is converged by a first converging lens 2 to produce a converged light beam 6 which is input to an optical fiber 3. The light beam issued at the output end 3a of the optical fiber 3 is focused by a second converging lens 4 so as to produce a focus point 8 to be applied on an object, which is a work piece to be worked or an affected part of a patient to be operated.

In such laser beam working apparatus or laser beam operating apparatus, the energy of the light beam focused by the second lens is directly utilized; thereby, it is necessary to monitor the level of the focused laser light. The above-mentioned way of monitoring the laser output power has been made by measuring the current of the laser oscillator tube and calculating the output power using that measured current. Another way of monitoring is made by providing a movable mirror between the output end of the laser oscillator and the first focusing lens, when measuring laser power, thereby reflecting the laser light by the mirror and give it to a laser power detector. Both of the above-mentioned monitoring means only monitors the output power of the laser oscillator and not the laser power to be irradiated on the object 8 from the hand piece 9.

When an optical fiber is utilized as a laser light waveguide in a laser light working apparatus or laser light operation apparatus, the output power of the laser light is as large as, for instance, 40 W or sometimes more, and such high power laser light will considerably heat the optical fiber, thereby the optical fiber is liable to deteriorate or age as time lapses. Thus, the laser light output from the hand-piece will decrease as time lapses while the output power from the laser oscillator does not decrease as much. Furthermore, when the optical fiber is broken at the midst thereof, the light beam is not irradiated from the hand-piece at all, while the monitored output level based on the above-mentioned measurement does not change. Therefore, the laser light output monitoring at the end of the laser light oscillator 1 does not constitute a reliable monitoring system. When the laser light power is monitored by providing the mirror to guide the laser light to the detector, the laser light is reflected by the mirror and is not inputted to the optical fiber. Therefore the above mentioned monitoring method is neither convenient nor reliable.

SUMMARY OF THE INVENTION

The present invention is to provide an improved irradiated power monitoring system for optical fibers which can measure the laser light output to be radiated from the hand-piece as such. In the irradiated power monitoring system for optical fibers in accordance the present invention, the light detection is made in the hand-piece which is at the output end of the optical fiber by providing light detecting means around the light path in the hand piece, so as to detect the outskirt part of the laser light, which part is not converged on the object. By such a monitoring system, the laser light emitted from the hand piece as such can be monitored and measured continuously and thereby the reliability of monitoring or measuring is very high.

The irradiated power monitoring system for optical fiber in accordance with the present invention comprises:

a light detector for detecting the outskirts light which is outside a cone shaped region of light emanating from an output end of the optical fiber, the light within the cone shaped region to be directed to an object for working.

DESCRIPTION OF THE PREFERRED EMBODIMENTS

Figure 1:
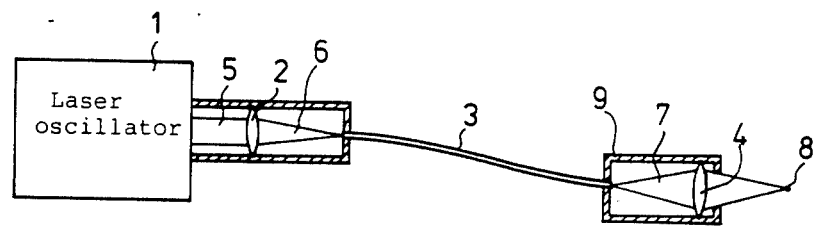
FIG. 1 is a schematic side view of the inventor's prior experiment which was not disclosed to the public.
Figure 2:
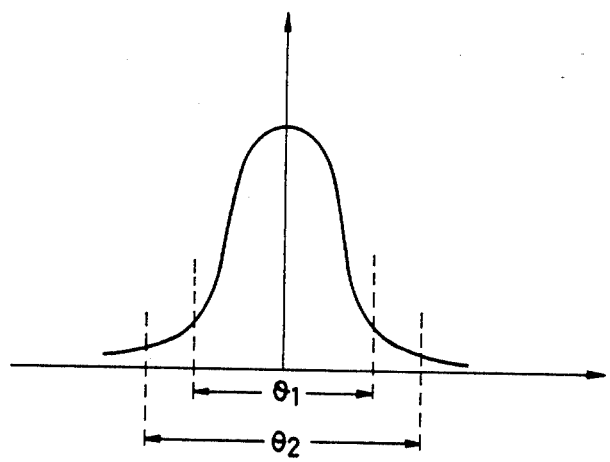
FIG. 2(a) is a graph showing the relation between the angles of light from the output end of the optical fiber 3 and the relative energy intensity thereof.
FIG. 2(b) is a side view illustrating the angle of FIG. 2(a).
Figure 2:
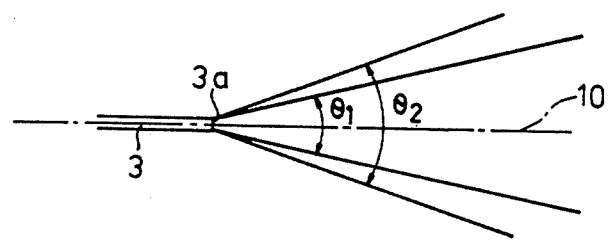

When the laser light is emitted from the output end of the fiber 3, the output light irradiates divergently as shown in FIG. 2(b) and the energy distribution is as shown in FIG. 2(a). That is, the energy distribution decreases rapidly as the angle from the optical axis increases; and at around a certain angle of $\theta_1$ the decrease becomes moderate, and when the angle $\theta$ becomes larger than $\theta_2$ almost all of the energy of the light is included within the wider angle $\theta_2$. Now provided that 90% of the emitted light lies within the range of angle $\theta_1$ and that 95% of the light energy is included in the range of angle $\theta_2$, then the diameter of the second lens 4 differs greatly between a first choice where only 90% of the light energy is taken out through the lens and a second choice where 95% of the light energy is taken out through the lens 4. That is, increasing the light energy to be taken out to the lens by 5% will require a considerable increase of lens diameter. In one example, if $\theta_1$ is 15° and $\theta_2$ is 30°, and distance from the output end of the optical fiber 3 to the center of the second lens is 4 cm, then the diameter of the lens for taking 90% light energy is 1 cm, while the diameter of the lens for taking out 95% of the light energy becomes 2 cm. The diameter of the lens should be limited to a reasonable diameter in view of easy handling and light weight and reasonable cost of the hand piece. Therefore, in the above-mentioned example, the lens diameter of 1 cm is preferable. But in this case, about 10% of the light energy is wasted without utility by converging by the lens. Thus, in an actual hand-piece, light energy of a certain percentage is always wasted. The present invention purports to utilize this outskirt part of the energy i.e., hitherto wasted light by receiving the outskirt portion of the light by a light detector for monitoring the output light energy.

Figure 3:
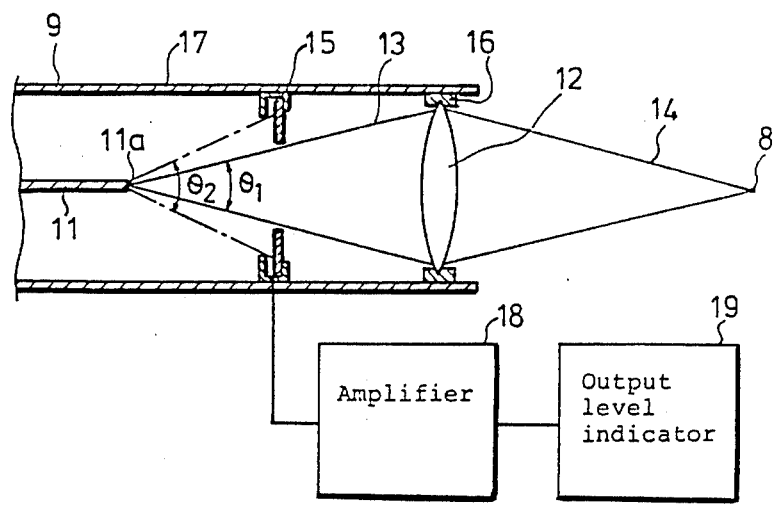
FIG. 3 is a side sectional view of a principal part of the hand-piece provided at the end of the optical fiber together with relevant circuit blocks.

Now, preferred embodiments are elucidated in detail referring to the drawings FIG. 3 and thereafter. FIG. 3 shows a principal part of the hand piece provided at the output end 11a of an optical fiber 11. The hand piece 9 has a housing 17 which has a second converging lens 12 disposed at the end of the housing 17, and a light detector 15 disposed between the output end 11a and the second lens 12. The second lens 12 is fixed to the housing by a lens holder 16. As shown in FIG. 3, the light detector 15 is disposed inside the housing coaxially around the optical axis of the hand-piece and around a maximum angle path 13 of laser light, in a manner not to touch the maximum angle path 13, but at close proximity thereto. The output of the light detector 15 is led to an amplifier 18 and further to an output level indicator 19.

Laser light emitted from the output end 11a of the optical fiber 11 has most of its light energy in the angle $\theta_1$ of the light locus, and only a small part of its energy is included in the outskirt of the light between the angle $\theta_2$ and angle $\theta_1$. The light of the outskirt part irradiates the light detector 15. The light energy is absorbed in the light detector 15 and converted to another kind of energy, for instance, heat energy and thereby produces an output signal. The light detector, for instance, issues an electric signal corresponding to heat energy generated by absorption of the outskirt portion of the light. Since the ratio of the light of the outskirt portion and the light within the angle $\theta_1$ can be measured by other measuring methods prior to installing the fiber into the hand-piece, the light energy contained in the angle $\theta_1$ can be known. Therefore, by multiplying the output signal of the light detector by the amplifier 18, the light energy within the angle $\theta_1$ can be calculated and the energy is indicated in the output level indicator 19. Since the outskirt portion of the light is continuously measurable all the time, the output level indicator 19 indicates the level of the output light to be applied on a work piece or an affected part continuously, without substantial loss of usable light or any inconvenience of utility due to temporal stopping of the light during measurement as in the conventional system.

Figures 4A, 4B:
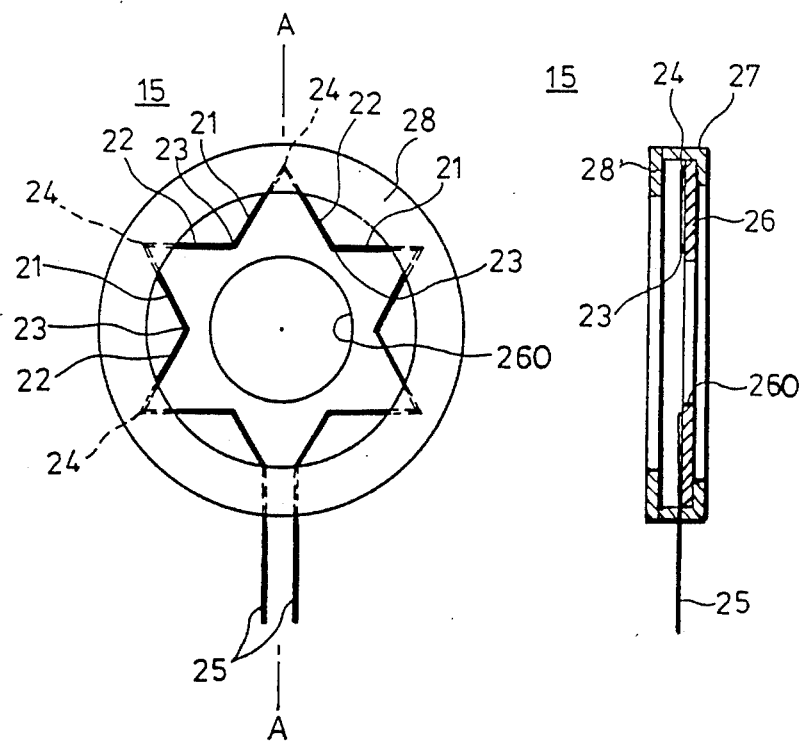
FIG. 4(a) is a front view of the light detector of the hand-piece shown in FIG. 3.
FIG. 4(b) is a side sectional view of the light detector of FIG. 4(a).
Figure 4:
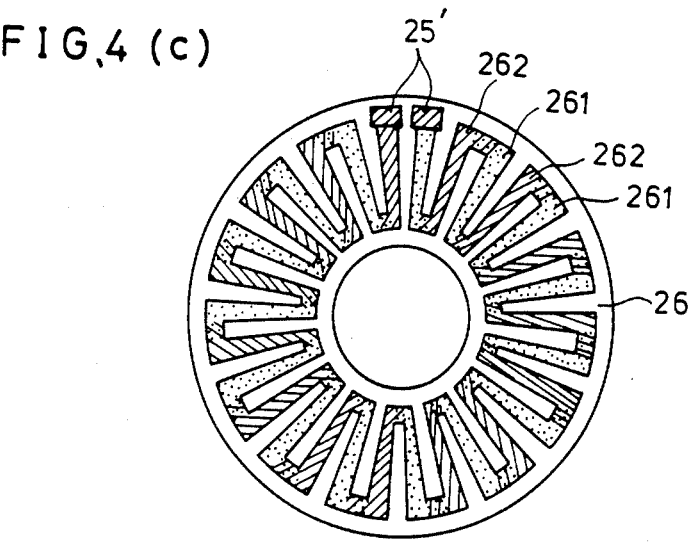
FIG. 4(c) is a front view of a modified example of a principal part of the light detector.

FIG. 4(a) and FIG. 4(b) show an example of the light detector. The light detector comprises a ring shaped housing 27, a substrate 26 of small thermal capacity having a hole 260 for passing light therethrough. The substrate 26 has a number of series connected thermocouples, preferably at least three, disposed with uniform pitch around the optical axis and constituting elementary wires 21, 21 . . . and 22, 22 . . . of a known thermocouple, for instance, copper wires and constantan wires. Outer junction points 24, 24 . . . are masked from the light by a ring shaped mask 28 disposed in front of the substrate. Both ends of the series connected thermo couples are led out by a pair of lead wires 25 to the amplifier 18. The inner junction points 23, 23 . . . are exposed to the outskirt light.

The above-mentioned configuration of circular and uniform disposition of a number of series connected thermo-couples is advantageous in producing averaged light detection output even though distribution of the light emitted from the output end 11a is not symmetrical with respect to the optical axis of the hand-piece. When the outskirt portion of the light irradiates the light detector 15, the inner junction points 23, 23 . . . receive light while the outer junction points 24, 24 . . . do not receive light; therefore, a temperature difference is produced between the inner junction points 23, 23 . . . and the outer junction points 24, 24 . . . , thereby producing an electric output in each thermo-couple. The sum of the output of the thermo-couples is issued, accordingly, across the lead wire 25.

Besides the above-mentioned copper-constantan thermo-couples, any other known thermo couples can be used. FIG. 4(c) shows another example of thermo-couples. This thermo-couple is made by vapor deposition of two kinds of metal films on a thin substrate. For easier understanding a first kind of metal films 261 are represented by dotted patterns and a second kind of metal films 262 are represented by hatched patterns.

Figure 5:
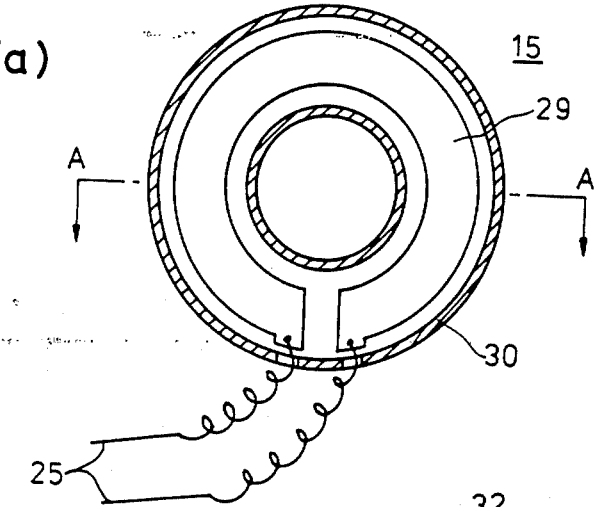
FIG. 5(a) is a front view of a modified example of a light detector.
FIG. 5(b) is a sectional view of the light detector of FIG. 5(a).
Figure 5:
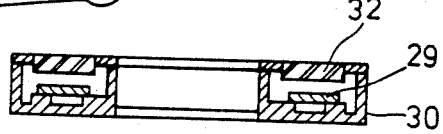

FIG. 5(a) and FIG. 5(b) show still another example of the light detector 15. This detector has a ring shaped housing 30 which has a transparent window 32 and a resistor 29 contained in the housing 30. The resistor 29 receives light through the window 32 and its temperature changes thereby changing the resistance across the lead wires 25. The resistor 29 is formed by a thin metal film or a thermistor material on a ring shaped substrate of insulating material. Or alternatively, the resistor 29 can be made by disposing a very fine platinum wire on the substrate with the surface of the platinum wire blackened so as to absorb the light efficiently. The light detector shown in FIG. 5(a) and FIG. 5(b) is also shaped in a ring, in order that, even though the emitted light from the output end 11a of the optical fiber has some irregularity around its optical axis, the light detection is averaged with respect to the optical axis. That is, by configuring the light detector in a ring shape, adverse effects of the irregularity with respect to the optical axis are eliminated, thereby the detected energy is substantially reliable.

The outskirt light from the output end 11a and incoming through window 32 and received by the resistor 29 is substantially absorbed by the resistor 29 and raises the temperature of the resistor 29. It thereby changes the resistance of the resistor 29 corresponding to the amount of input light. Therefore, by leading the electric output to the amplifier 18, the amount of output light can be indicated by the output level indicator 19.

Figure 6:
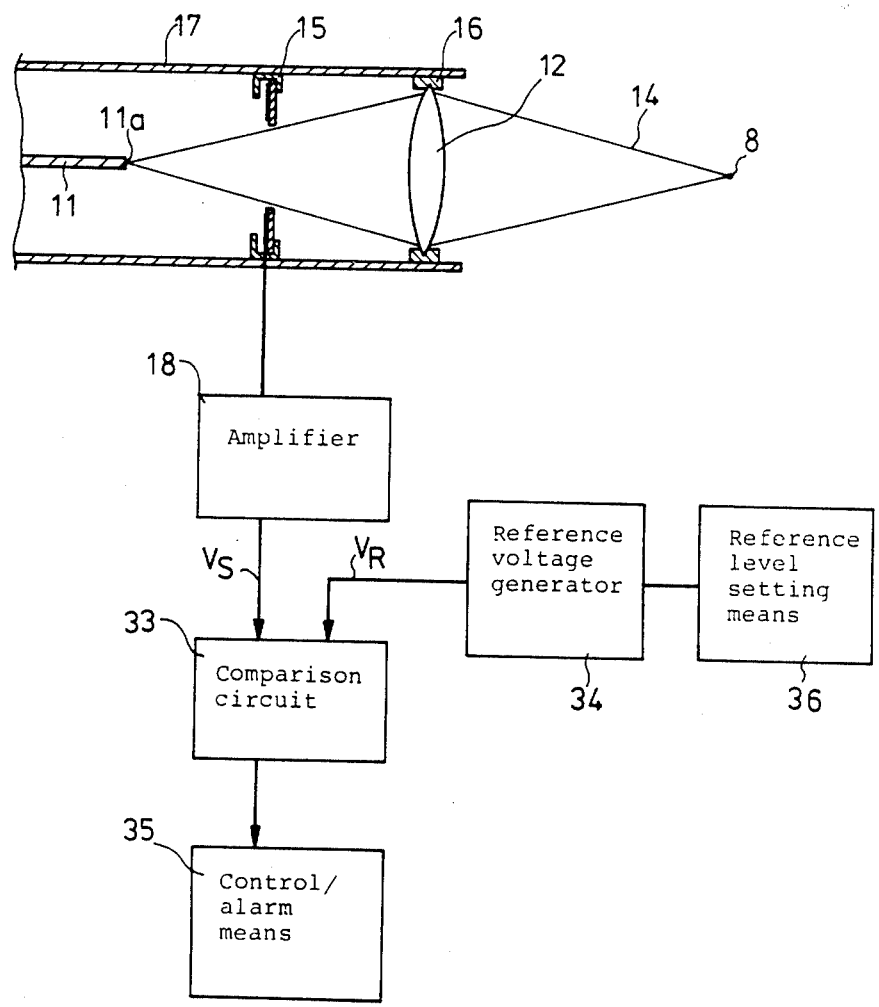
FIG. 6 is a sectional view of a hand-piece together with circuit blocks of another embodiment of the present invention.

FIG. 6 shows another example comprising a modified circuit configuration. The optical part is identical to the example of FIG. 3, and the electric circuit part has further a comparison circuit 33, control/alarm means 35, reference voltage generator 34 and a reference level setting means 36.

Provided that the optical fiber 11 emits a predetermined amount of light corresponding the level set by the reference level setting means 36, then the output of the light detector 15 is amplified and compared in the comparison circuit 33 with the output of the reference voltage generator 34, the output of which is set by the reference level setting means 36. Therefore, when the light output from the optical fiber 11 decreases, the comparison circuit 33 output to the control/alarm means 35 causes an alarm to issue. Therefore, when the optical fiber 11 is accidentally cut off or when attenuation of the light in the optical fiber 11 exceeds a predetermined level, then the alarm is issued. Accordingly, the user of the apparatus can know of the necessity to replace the optical fiber or modify or repair the apparatus.

As has been elucidated in detail in examples, according to the present invention, the output light as such from the hand-piece at the output end of the optical fiber can be reliably and accurately measured, thereby the apparatus as, for example, a laser working or as laser surgery operation becomes very much reliable. Furthermore, in the apparatus of the present invention, the watching or measurement can be made continuously without interrupting the laser working or laser surgical operation light, and substantial loss of the laser light. The present invention is applicable to all kinds of laser working apparatus and laser surgical operation apparatus. Furthermore, since the light detection is made by thermo-electric transducing, detection of any laser light beam, for instance, a laser light beam of YAG laser or of $CO_2$ laser, can be detected reliably.

What is claimed is:

1. An irradiated power monitoring and trouble monitoring system for a laser processing apparatus comprising:
    a laser light source,
    an optical fiber for transmitting laser light from said laser light source,
    light focussing means for focussing said laser light received from an output end of said optical fiber, and
    a light detector for detecting a marginal small portion of said laser light outside of a cone shaped emmission of said laser light from said output end of said optical fiber, said light detector being disposed between said output end of said optical fiber and said light focussing means.

2. An irradiated power monitoring system for optical fiber in accordance with claim 1, wherein said light detector comprises:
    at least three light detecting devices disposed at uniform intervals on the same plane through said cone and outside of said cone and connected to generate an output which corresponds to the sum of the said laser light detected by said light detecting devices.

3. An irradiated power monitoring system for optical fibers in accordance with claim 1, wherein said light detector comprises:
    a ring shaped light mask with a center hole having a diameter which is slightly larger than the cross-sectional diameter of said cone shaped light emission.

4. An irradiated power monitoring system for optical fibers in accordance with claim 1 or 2, wherein said light detector comprises:
    thermo-couples disposed on a ring shaped substrate, a hot junction of said thermo-couples being arranged at a center portion of said ring and a cold junction of said thermo-couples being arranged at a marginal part of said ring, and
    a substantially ring shaped light mask for shielding said cold junction of said thermo-couples.

5. An irradiated power monitoring system for optical fibers in accordance with claim 1 or 2, wherein,
    said light detector is a thin film resistance which changes resistance depending on its temperature.

6. An irradiated power monitoring system for optical fibers in accordance with claim 1, 2 or 3 comprising:
    comparison means for comparing the detected level of said laser light with a preset reference level, and
    alarm means for warning when the detected laser light level is lower than said reference level.

7. An irradiated power monitoring system for optical fibers in accordance with claim 3, wherein
    said light detector has a first kind of vapor deposited metal film regions and a second kind of vapor deposited film regions, both vapor deposited film regions extending radially on said substrate and being connected at inner and outer parts with an adjacent vapor deposited film region of a different kind of film.

* * * * *